United States Patent
Palkar et al.

(10) Patent No.: US 11,166,941 B2
(45) Date of Patent: Nov. 9, 2021

(54) SYNERGISTIC NUTRITIONAL COMPOSITIONS FOR ENHANCING ATP EFFICIENCY

(71) Applicant: CELAGENEX RESEARCH (INDIA) PVT. LTD., Maharashtra (IN)

(72) Inventors: Jotiram Palkar, Thane (IN); Rajendra Prasad Tongra, Jaipur (IN)

(73) Assignee: CELAGENEX RESEARCH (INDIA) PVT. LTD., Thane (IN)

( * ) Notice: Subject to any disclaimer, the term of this patent is extended or adjusted under 35 U.S.C. 154(b) by 0 days.

(21) Appl. No.: 17/140,949

(22) Filed: Jan. 4, 2021

(65) Prior Publication Data

US 2021/0196686 A1 Jul. 1, 2021

(30) Foreign Application Priority Data

Jan. 1, 2020 (IN) .............................. 201921044295

(51) Int. Cl.
| | |
|---|---|
| *A61K 31/4188* | (2006.01) |
| *A61P 43/00* | (2006.01) |
| *A61K 9/00* | (2006.01) |
| *A61K 31/194* | (2006.01) |

(52) U.S. Cl.
CPC ........ *A61K 31/4188* (2013.01); *A61K 9/0053* (2013.01); *A61K 31/194* (2013.01); *A61P 43/00* (2018.01)

(58) Field of Classification Search
CPC .............. A61K 31/4188; A61K 9/0053; A61K 31/194; A61K 36/00; A61P 43/00
USPC ....................................................... 424/725
See application file for complete search history.

(56) References Cited

U.S. PATENT DOCUMENTS

| | | | |
|---|---|---|---|
| 9,050,306 B2 | 6/2015 | Cash | |
| 10,016,385 B2 | 7/2018 | B. Cash | |
| 2007/0183996 A1* | 8/2007 | Okombi | A61K 8/42 424/62 |
| 2010/0150895 A1* | 6/2010 | Mazzio | A61K 31/7004 424/94.1 |
| 2013/0273557 A1* | 10/2013 | Gribkoff | A61K 49/0008 435/7.1 |

FOREIGN PATENT DOCUMENTS

| | | | |
|---|---|---|---|
| EP | 3056199 A1 | | 8/2016 |
| JP | H0995448 A | | 4/1997 |
| KR | 1020160015174 | * | 2/2016 |
| WO | 2011148014 A1 | | 12/2011 |
| WO | 2011163319 A2 | | 12/2011 |
| WO | 2014016003 A1 | | 1/2014 |

OTHER PUBLICATIONS

Gould, "Salt Selection for Basic Drugs", International Journal of Pharmaceutics, 1986, vol. 33, Issues 1-3, pp. 201-217.*
Andrea T. Da Poian "Nutrient Utilization in Humans: Metabolism Pathways" Nature Education 3(9):11, 2010.
Denizot et al. "Rapid colorimetric assay for cell growth and survival. Modifications to the tetrazolium dye procedure giving improved sensitivity and reliability" J Immunol Methods; 1986; 89: 271-277].
Heather Wilkins et al. "Oxaloacetate activates brain mitochondrial biogenesis, enhances the insulin pathway, reduces inflammation and stimulates neurogenesis" Hum Mol Genet. Dec. 15, 2014; 23(24): 6528-6541.
Kiyohiko Yoshikawa "Studies on Anti-diabetic Effect of Sodium Oxalcacetate" Tohoku J. Exp. Med., 1968, 96, p. 127-141.
Krebs "The effect of inorganic salts on the ketone decomposition of oxaloacetic acid" Biochem. 1942, 36, p. 303-05.
Sone et al. "Biotin enhances ATP synthesis in pancreatic islets of the rat, resulting in reinforcement of glucose-induced insulin secretion" Biochem Biophys Res Commun. Feb. 13, 2004; 314(3):824-9.
Imamura et al."Visualization of ATP levels inside single living cells with fluorescence resonance energy transfer-based genetically encoded indicators" Proc Natl Acad Sci USA; 2009; 106:15651-15656.
J.T. Millard "Exercise Physiology" Jan. 2013.
Berg JM, et al. 2002 Biochemistry, 5 Edition.

* cited by examiner

*Primary Examiner* — Sahar Javanmard
(74) *Attorney, Agent, or Firm* — Maschoff Brennan (57) ABSTRACT

The invention disclosed herein relates to synergistic nutritional compositions for enhancing cellular ATP efficiency. Particularly, the invention relates to a synergistic, efficient, nutritional composition for promoting cellular ATP production comprising a therapeutically active exogenous combination of a stabilized oxaloacetate and a biotin-manganese complex along with pharmaceutically acceptable excipients; wherein the stabilized oxaloacetate and the biotin-manganese or salts thereof are present in a weight ratio ranging from 1:0.01 to 1:0.2. Further, the present synergistic nutritional composition is useful for treating ATP deficiency disorders, age-related metabolic disorders, neurodegenerative diseases, cardiovascular diseases, bone related disorders, central nervous system diseases, cognitive disorders and like thereof.

10 Claims, 5 Drawing Sheets

SYNERGISTIC NUTRITIONAL COMPOSITIONS FOR ENHANCING ATP EFFICIENCY

TECHNICAL FIELD

The present invention relates to synergistic nutritional compositions for enhancing intracellular ATP production or efficiency. Particularly, the invention provides synergistic compositions comprising a therapeutic exogenous blend of stabilized oxaloacetate (OAA) and biotin-manganese (biotin-Mn) complex for increasing mitochondrial ATP turnover. Further the present synergistic nutritional composition is useful for treating ATP deficiency disorders, age-related metabolic disorders, neurodegenerative diseases, cardiovascular diseases, bone related disorders, central nervous system diseases, cognitive disorders and like thereof.

BACKGROUND AND PRIOR ART

Carbohydrates, lipids, and proteins are the major constituents of food and serve as fuel molecules for the human body. The digestion of these nutrients in the gastrointestinal tract and the subsequent absorption (entry into the bloodstream) of the digestive end products make it possible for tissues and cells to transform the potential chemical energy of food into useful work.

'Energy metabolism' is the general process by which living cells acquire and use the energy needed to stay alive, to grow, and to reproduce. Particularly, the energy is released through breaking of chemical bonds of nutrient molecules. The nutrients get oxidized and form high-energy compounds, particularly ATP, which work as the main chemical energy carrier in all cells [Andrea T. *Da Poian Nature Education* 3(9):11, 2010].

The breakdown and synthesis of carbohydrates, proteins, and lipids connect with the pathways of sugar catabolism. The simple sugars such as glucose, galactose, fructose, glycogen, and pentose are catabolized during glycolysis. The amino acids from proteins connect with glucose catabolism through pyruvate, acetyl CoA, and intermediates of the TCA cycle.

The TCA cycle is the heart of energetic metabolism of the cell, i.e., almost all pathways of the energetic metabolism are connected to the TCA cycle. For example, ETC (electron transport chain), gluconeogenesis, transamination, oxidative phosphorylation, chemiosmosis, deamination of amino acids or lipogenesis. Moreover, it is considered as the cellular source of amphibolic pathways. The TCA cycle is crucial for the cell to regulate concentrations of metabolites in the mitochondria, wherein anaplerotic flux balances cataplerotic flux in order to retain homeostasis of cellular metabolism.

TCA cycle is the cell's metabolic hub, since it not only generates energy but also consumes and produces metabolites relevant to hosts of other processes. It is called a "cycle" because it both begins and ends with the key substrate—i.e., oxaloacetate. The TCA cycle occurs inside the mitochondria and generates a pool of chemical energy (ATP, NADH, and $FADH_2$, another electron carrier) from the oxidation of pyruvate.

The total number of ATP molecules produced from glycolysis and citric acid cycle along with the number of ATP molecules produced in the ETC yields 30 ATP molecules per molecule of glucose [*Exercise Physiology* J. T. Millard 2013].

It has been observed that ATP levels in the blood slowly decrease over a period of time due to factors like age, exercise or injury. There are two processes which provide intracellular replenishment of ATP viz. oxidative (aerobic) phosphorylation and anaerobic phosphorylation.

Moreover, oxidative phosphorylation is a process, where electron transport from the energy precursors from the citric acid cycle leads to the phosphorylation of ADP, thereby producing ATP which is the basic unit of energy for metabolic processes.

In view of the recognized importance of maintaining or restoring a normal mitochondrial or cellular function or enhancing the cellular respiration, the quantum of energy production (ATP) is highly required.

The TCA cycle is the major degradative pathway for the generation of ATP. The TCA cycle operates to a reduced extent unless new intermediates are formed. However, the recycled intermediates are detected less to generate more energy carriers of ATP.

ATP is the main energy source for majority of all the cellular functions. It must be constantly regenerated, because without adequate ATP, human cells cannot function properly. Therefore, there is a need to increase the availability of TCA cycle substrates which subsequently gives higher yield of ATP.

Oxaloacetate is central to energy use in all known living things. It is an important intermediate or key substrate of TCA cycle, which releases energy stored in carbohydrates, fats, and proteins. 'Oxaloacetate' is one of the essential dicarboxylic organic intermediate molecules of metabolic citric acid cycle, which is part of the body's energy production and waste management systems. It is essential in infant development. A genetic deficiency in the enzymes that make oxaloacetate will cause a serious neurological disease and developmental delays.

Oxaloacetate (OAA) is a bioenergetic medicinal agent, which increases cell energy levels. Further oxaloacetate reportedly reduces hyperglycemia in type II diabetes and extends longevity. Some researchers have tested the medicinal use of oxaloacetate in seizure, cancer, stroke, and traumatic brain injury.

Some other useful therapeutic applications of oxaloacetate are reported in the art.

WO2011163319A2 relates to oxaloacetate compounds that activate AMP-activated protein kinase (AMPK), and the use of the compounds in the prevention or treatment of disorders such as diabetes, metabolic syndrome, obesity, cardiovascular disease, Alzheimer's disease, and cancer. WO2011148014A1 relates to the use of oxaloacetate in the treatment of ischemia. U.S. Ser. No. 10/016,385B2 discloses pharmaceutically effective amount of a composition of oxaloacetate for use in the treatment of cancer.

Further WO2018/057737A1 relates to methods for treating symptoms of premenstrual syndrome (PMS) and premenstrual dysphoric disorder (PMDD) through administration of a pharmaceutical composition comprising oxaloacetate, oxaloacetate salts, oxaloacetic acid and/or anhydrous enol-oxaloacetate.

Cell studies with oxaloacetate have also shown that oxaloacetate can increase muscular endurance by up to 10%, by providing extra energy to the cells, it also significantly increases lifespan. Further, it facilitates blood sugar level stabilization and maintains glucose homeostasis.

The administration of additional oxaloacetate shows favorable metabolic changes such as promotion of brain mitochondrial biogenesis, activation of the insulin signaling pathway, reduction in neuroinflammation and activation of hippocampal neurogenesis. [*Hum Mol Genet.* 2014 Dec. 15; 23(24): 6528-6541].

A nutritional supplement called BenaGene™ consisting of oxaloacetic acid is used for improving brain health and cognitive function. Oxaloacetate has been found to help protect brain neurons and brain mitochondrial DNA and provide potent antioxidant protection.

In the past, numerous efforts and experiments have been conducted to establish stable formulation of oxaloacetate suitable for oral administration.

Kiyohiko Yoshikawa [*Tohoku J. Exp. Med.,* 1968, 96, p 127-141] discloses the anti-diabetic effect of sodium oxaloacetate. Krebs [*Biochem.* 1942, 36, p 303-05] has reported that multi-valent cations such as Al, Cu, Fe II, Fe III, etc., catalyse the ketone decompositions of oxaloacetic acid. The cations do not stabilize alpha ketonic-dicarboxylic acids.

It is observed that temperature, pH, metal ions (Cu, Fe) and interaction with amines have strong impact on the decomposition rate of oxaloacetate.

EP3056199A1 provides a non-biodegradable oxaloacetate composition which comprises an oxaloacetic acid in combination with one or more components selected from a group of a hygroscopic pH modifier, a hygroscopic taste modifier, a hygroscopic binding agent, and a hygroscopic release agent.

Additionally, U.S. Pat. No. 9,050,306B2 discloses a method to prevent the degradation of oxaloacetic acid by creating an anhydrous enol-oxaloacetate and isolating the anhydrous enol-oxaloacetate with water content less than 2% from moisture with a sealed encapsulation.

Notably, oxaloacetate not only provides the building blocks needed for the TCA cycle to produce ATP energy, but in fact promotes mitochondrial biogenesis—i.e., helps new mitochondria form within cells and boosts energy production in the body. The key benefits of oxaloacetic acid can be summarized as anti-aging, increasing lifespan (life extension), and improving brain health, blood sugar regulation, and energy production.

In view of the above, oxaloacetate is a critical component in producing ATP which should be substantially replenished to carry on better functioning of the TCA cycle and electron transport chain.

As oxaloacetic acid gets exhausted during cellular metabolism, the need arises to provide additional oxaloacetate exogenously to modulate cellular function.

Intriguingly, 'oxaloacetate' is formed by the carboxylation of pyruvate, in a reaction catalyzed by biotin-dependent enzyme pyruvate carboxylase which plays a crucial role in gluconeogenesis.

It is active only in the presence of acetyl CoA, which signifies the need for more oxaloacetate. If the energy charge is high, oxaloacetate is converted into glucose. If the energy charge is low, oxaloacetate replenishes the citric acid cycle. [Berg J M, et al. 2002 *Biochemistry,* 5 Edition].

Further, oxaloacetate, is the principal substrate for gluconeogenesis. Gluconeogenesis is an important fate of amino acid carbon skeletons in the fasting state, when the metabolic imperative is to maintain a supply of glucose for the central nervous system and red blood cells.

In order to provide glucose for vital functions such as the metabolism of RBCs and the CNS during periods of fasting (greater than about 8 hours after food absorption in humans), the body needs a way to synthesis glucose from precursors such as pyruvate and amino acids. The gluconeogenesis occurs in the liver and kidney.

The important point now is that citric acid cycle intermediates must be replenished if any are drawn off for biosynthesis. If high amounts of oxaloacetate are converted into amino acids for protein synthesis, the energy needs of the cell rise subsequently. The citric acid cycle will operate to a reduced extent unless new oxaloacetate is formed, because acetyl CoA cannot enter the cycle unless it condenses with oxaloacetate. Even though oxaloacetate is recycled, a minimal level must be maintained to allow the cycle to function.

The metabolic pathways ascertain oxaloacetate formation from pyruvate by a carboxylation reaction which is catalyzed by biotin-dependent enzyme pyruvate carboxylase. The synthesis of oxaloacetate by the carboxylation of pyruvate is anaplerotic reaction. Anaplerosis is the act of replenishing TCA cycle intermediates that have been extracted for biosynthesis.

If oxaloacetate is removed from the TCA cycle for glucose synthesis, it must be replaced. If there is not enough oxaloacetate available to form citrate, the rate of acetyl CoA metabolism, and hence the rate of formation of ATP, will slow down.

Normally, excess pyruvate is shunted into gluconeogenesis via conversion of pyruvate into oxaloacetate, but because of the enzyme deficiency, excess pyruvate is converted into lactate instead.

Pyruvate carboxylase (PC) is a mitochondrial enzyme bound to biotin that catalyzes the conversion of pyruvate to oxaloacetate when abundant acetyl CoA is available, replenishing Krebs cycle intermediates in the mitochondrial matrix.

Pyruvate carboxylase (PC) is a biotin-dependent mitochondrial enzyme that catalyzes the ATP-dependent carboxylation of pyruvate to oxaloacetate and replenishes Krebs cycle intermediates in the mitochondrial matrix.

Moreover, pyruvate to oxaloacetate reaction proceeds via the removal of a proton from pyruvate, by an active site residue, to generate an enolate intermediate. The enolate intermediate then attacks $CO_2$ transiently released from pyruvate carboxylase linked biotin molecule and releases oxaloacetate. The biotin molecule is protonated by the active site residue and released from the active site of the pyruvate carboxylase domain to be re-carboxylated.

Biotin is an essential biochemical, which acts as a carrier for carbon dioxide in the pyruvate carboxylase reaction.

Biotin, also known as vitamin H or B7, is one of the essential vitamins for maintaining and boosting body functions, including metabolism, and supporting good weight control. Biotin is vital for the health of human bones, skin and nails, as well as for keeping liver and nervous system functioning properly. Biotin enhances ATP synthesis in pancreatic islets, resulting in reinforcement of glucose-induced insulin secretion [*Biochem Biophys Res Commun.* 2004 Feb. 13; 314(3):824-9]WO2014016003A1 relates to the use of biotin for treating multiple sclerosis, with effective dosage of 100 and 300 mg.

JPH0995448A discloses a composition of oligosaccharides and biotin for preventing obesity, diabetes, dermatitis, conjunctivitis, muscle ache and fatigue conditions.

Biotin also known as vitamin B7, is a vital part of a healthy metabolism and creating important enzymes and is used by the body to metabolize carbohydrates, fats and amino acids.

It is reported that the major biological function of biotin is to act as a covalently bound cofactor for the biological activities of mammalian biotin-dependent carboxylases. These biotin-dependent carboxylases have a crucial role in essential biological processes such as fatty acid synthesis, gluconeogenesis, and amino acid metabolism. Humans cannot synthesize biotin. However, protein rich food makes biotin available for absorption through gut bacteria.

In view of the need of replenishment of sufficient oxaloacetate for energy production, the present inventors have performed rigorous studies and trials and developed a synergistic composition which not only enriches mitochondrial oxaloacetate production but also ameliorates cytosolic concentration of oxaloacetate without any artificial or synthetic drug intervention. The inventors have successfully demonstrated an increase in intracellular ATP turnover through consumption of the present synergistic combination. Moreover, the present inventors have developed an advanced nutritional therapy for improving synthesis of ATP as an energy supplementation.

Objective

The primary objective of the invention is to provide a nutrient based energy source for cellular maintenance.

Another objective of the invention is to provide a cost effective, nutritional composition of organic, non-toxic, bioenergetic compounds that effectively improves the metabolic pathway of cellular respiration.

A further objective of the invention is to provide a stable, nutritional composition for improving NAD pool level.

Another objective of the invention is to provide a synergistic nutritional composition of bioenergetic compounds for enhancing intracellular ATP production.

Yet another objective of the invention is to provide a nutritional composition with active moieties which synergistically enhance cellular energy production (ATP) by establishing anaplerosis.

A further objective of the invention is to provide a novel, stable, nutritional composition of vitamin-mineral complex of dicarboxylic acid for improving cellular energy production.

Another objective of the invention is to provide a novel, potent nutritional composition of vitamin based TCA cycle substrates for treating age-related metabolic disorders or dysfunctions through site specific action with no adverse effects.

SUMMARY

To meet the above objectives, the inventors of the instant invention have carried out thorough experiments to establish a synergistic combination of bioactive ingredients or nutritional supplements or dietary supplements or micronutrients or natural substances or metabolic intermediates or bioenergetic agents or biochemicals or organic molecules or TCA intermediates that ameliorate intracellular energy efficiency in a subject in need thereof.

In a primary aspect, the invention relates to a stable, potent, therapeutically active, nutritional composition comprising exogenous blend of a TCA intermediate and a vitamin-mineral complex that significantly improves metabolic energy efficiency.

In a preferred aspect, the invention provides stable, nutritional compositions that enhance the output of cellular respiration by fostering therapeutic amounts of coenzyme mediated TCA cycle substrate or intermediate.

In another aspect, the invention provides a synergistic combination of exogenous TCA cycle intermediates with a vitamin-mineral complex for improving cellular function, wherein the vitamin-mineral complex is a Biotin-Manganese (Biotin-Mn) complex and the TCA cycle intermediate is Oxaloacetate (OAA).

In one aspect, the administration of effective amount of exogenous Biotin-Mn complex enriches inner mitochondrial production of oxaloacetate through pyruvate corboxylation, and exogenous oxaloacetate ameliorates depleted cytosolic concentration of oxaloacetate.

In another aspect, the invention provides that the present compositions not only proliferate intracellular ATP turnover but also enhance gluconeogenesis metabolic process from non-carbohydrate precursors.

In yet another particular aspect, the invention provides a combination therapy, wherein oxaloacetate or pharmaceutically acceptable salts thereof is administered along with biotin-Mn complex, and wherein the combination provides significant therapeutic efficacy that is higher than the efficacy of either active ingredient administered alone.

In another aspect, the invention provides that the instant composition enriches cellular density of oxaloacetate through synergistic anaplerotic effect.

In another aspect, the instant invention offers a nutritional composition that comprises oxaloacetate in a specific or therapeutically effective amount, wherein the oxaloacetate works synergistically with the biotin-manganese complex to increase the ability of a plurality of mitochondria in a cell to synthesize adenosine triphosphate (ATP).

In yet another aspect, the invention relates to synergistic nutritional compositions comprising a combination of oxaloacetate salt in a range of 1-500 mg [equivalent to oxaloacetic acid], biotin in a range of 10 to 10000 mcg and cofactor Mn in the form of amino acid chelate in a range of 1 to 100 mg; along with pharmaceutically acceptable excipients/carriers.

In a further aspect, the synergistic combination of oxaloacetate and biotin-manganese complex enhances the oxidation of NADH to $NAD^+$ resulting in increase in the production of ATP.

In one more aspect, the instant nutritional composition is useful for treating age-associated metabolic disorders, neurodegenerative diseases, cardiovascular diseases, bone related disorders, CNS disorders, insulin restriction, obesity, premenstrual syndrome, cognitive disorders, cancer, insulin resistance, diabetes and like thereof.

Abbreviations:
OAA: Oxaloacetate
ATP: Adenosine triphosphate
ADP: Adenosine diphosphate
AMP: Adenosine monophosphate
NAD+: Nicotinamide Adenine Dinucleotide (oxidized)
NADH: Nicotinamide Adenine Dinucleotide (reduced)
TCA: Tricarboxylic acid cycle
Mn-biotin: Manganese-biotin
PC: Pyruvate Carboxylase
NADP+: Nicotinamide adenine dinucleotide phosphate
CNS: Central nervous system

BRIEF DESCRIPTION OF FIGURES

FIG. 1 illustrates the pyruvate to oxaloacetate metabolic pathway

FIG. 2 illustrates the oxaloacetate transport through shuttle pathway

DETAILED DESCRIPTION

The invention will now be described in detail in connection with certain preferred and optional embodiments, so that various aspects thereof may be more fully interpreted and comprehended. However, any skilled person in the art or artisan will appreciate the extent to which such embodiments could be generalized in practice.

It is further to be understood that all terminology used herein is for the purpose of describing particular embodiments only, and is not intended to be limiting in any manner or scope.

Unless defined otherwise, all technical and scientific expressions or terms used herein have the same meaning as commonly understood by one of ordinary skill in the art to which embodiments of the invention pertain.

In describing and claiming the embodiments of the present invention, the following terminology will be used in accordance with the definitions set out below which are known in the art.

The singular forms "a," "an," and "the" include plural reference unless the context clearly dictates otherwise. Also the term 'composition' does not limit the scope of the invention it may include multiple compositions illustrations to establish best mode of the invention.

The term "pharmaceutically/nutraceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Particularly the term "pharmaceutically-acceptable salts" refers to relatively non-toxic, inorganic and organic acid addition salts of compounds, alkali or alkaline earth metal salts, as well as solvates, co-crystals, polymorphs, isomers, enantiomers, congeners and like thereof.

The term used herein 'tricarboxylic acid cycle' (TCA cycle) can be interchangeable with Krebs cycle, citric acid cycle (CAC), metabolic pathway, without making any difference.

In one preferred embodiment, the invention provides a novel, stable, potent, therapeutically active nutritional composition comprising vitamin-mineral complex mediated TCA intermediate for enhancing output of cellular energy.

Moreover, the instant nutritional composition increases availability of the exogenous substrate and vitamin inputs for the TCA cycle to obtain significant output of energy, wherein the inputs are TCA intermediate i.e., dicarboxylic acid ester and vitamin-mineral complex and the output is energy in the form of adenosine triphosphate (ATP).

Further, the invention provides a non-toxic, safe, nutritional composition of bioenergetic compounds for restoring the quality of aged cells or damaged cells endured by anaplerosis.

In another embodiment, the invention provides bioenergetics intervention comprising metabolic and enzymatic processes that lead to production of energy in the form of adenosine triphosphate (ATP) molecules.

In another embodiment, the invention relates to a nutritional composition comprising a synergistic combination of a TCA cycle substrate and a vitamin-mineral complex in a specific amount along with pharmaceutically acceptable salts or carriers.

In a further embodiment, the invention relates to a nutrient enriched composition comprising a combination of bioenergetic agents, wherein the bioenergetic agents are TCA cycle substrate and vitamin-mineral complex and wherein the TCA cycle substrate is oxaloacetate (OAA) and vitamin-mineral complex is biotin-Manganese complex. The combination synergistically improves intracellular energy (ATP) pool through anaplerosis.

According to the invention, the administration of exogenous oxaloacetate provides a substrate for regulating citric acid cycle. The ability to regulate the cycle keeps the cell in a stable state and avoids loss of metabolic energy.

'Oxaloacetic acid' is a crystalline organic compound with the chemical formula $C_4H_4O_5$. This acid is also known as '2-Oxosuccinic acid', 'Ketosuccinic acid', 'Oxobutanedioic acid' or '3-carboxy-3-oxopropanoic acid'. Oxaloacetic acid, also known as keto-oxaloacetate or 2-oxobutanedioate, belongs to the class of organic compounds known as short-chain keto acids and derivatives and is represented by Formula I below.

Oxaloacetic acid, in the form of its conjugate base is called oxaloacetate and is represented by Formula II above. Oxaloacetate is a metabolic intermediate in many processes that occur in animals. Oxaloacetic acid can be derived from oranges, apples, bananas, peas, taters, and green spinach in low concentration. Oxaloacetic acid is highly water soluble and oxaloacetate is a water soluble ion of oxaloacetic acid. Oxaloacetate improves the metabolic pathways in various ways.

According to the instant invention, the therapeutically effective amount of oxaloacetate present in the composition ameliorates depleted cytosolic concentration of oxaloacetate that subsequently increases cellular NAD+level.

The conversion of oxaloacetate to malate is an energy favorable reaction in the cells that promotes conversion of NADH to $NAD^+$. In the mitochondria, the electron transport chain is a major contributor to NADH oxidation into NAD+, coupling this reaction to ATP synthesis.

In another embodiment, the invention provides that additional or exogenic oxaloacetate regulates the intracellular NAD pool, which is essential for mitochondrial function, cell viability and ATP levels. NAD functions through the activation of a transcription cascade that results in increased expression of mitochondrial proteins involved in ATP production. Notably, the significant density of OAA regulates concentrations of TCA cycle metabolites in the mitochondria through synergistic anaplerotic effect.

In another embodiment, the oxaloacetate employed in the composition is used in the stabilized form, wherein the oxaloacetate is either in the form of the corresponding acid, alkyl protected oxaloacetic acid, thermally stable oxaloacetic acid, or metal ion salts thereof. The metal ion is selected from Na, K, Li. Further to improve the stability of OAA, few antioxidants or stabilizers are optionally added in the composition. In a preferred embodiment, the antioxidants are selected from the group consisting of ascorbic acid, n-propyl gallate, α-tocopherol and like thereof.

In yet another embodiment, the invention provides a synergistic nutritional composition comprising a therapeutically effective amount of oxaloacetate or salts thereof present in a range of 1-500 mg of equivalent oxaloacetic acid of total composition.

In another preferred embodiment, the invention affords a synergistic composition for augmentation of ATP through mitochondrial anaplerotic effect, wherein the mitochondrial inducer is a vitamin-mineral complex. In an embodiment, the vitamin-mineral complex is biotin-manganese complex.

Biotin also called as vitamin H or vitamin B7, belongs to the group of B vitamins. It is a water-soluble vitamin which helps metabolize substances including fatty acids and glucose and convert food into caloric energy. Biotin is stable at room temperature. Foods that contain biotin are peanuts, yeast, egg yolks, raspberries, bananas, pork, avocado, broccoli, sweet potatoes cauliflower, spinach, milk, bananas, nuts, grains, and liver.

Biotin is important in several essential metabolic reactions in humans, such as catalyzing the synthesis of fatty acids, metabolism of the amino acid leucine, and gluconeogenesis. Biotin is important in cell growth and plays a role in the Krebs cycle.

Biotin has the chemical formula $C_{10}H_{16}N_2O_3S$ and is represented by Formula III below. Biotin is composed of an ureido (tetrahydroimidizalone) ring fused with a tetrahydrothiophene ring, which is an organic compound consisting of a five-membered ring containing four carbon atoms and a sulfur atom.

(III)

Biotin

According to the invention, the administration of exogenous biotin-manganese complex enriches inner mitochondrial production of OAA through pyruvate carboxylation by catalyzing pyruvate carboxylase.

In another embodiment, the invention provides an ATP enhancing composition comprising biotin, wherein biotin acts as a $CO_2$ carrier or shuttler. It is the major cofactor involved in carbon dioxide metabolism.

Particularly, biotin moiety acts as a swinging arm to transport carbon dioxide to the catalytic site of pyruvate carboxylase that eventually increases expression of pyruvate carboxylase for production of oxaloacetate inside the mitochondria. The active side pyruvate carboxylase enzyme catalyzed reaction replenishes the supply of intermediates in the citric acid cycle when intermediates are removed for different biosynthetic purposes. (essentially to provide oxaloacetate). In short, pyruvate carboxylase plays an anaplerotic role. By producing oxaloacetate, this enzyme helps to replenish an important TCA intermediate, and also opens the way for gluconeogenesis from pyruvate and other compounds that are converted to pyruvate such as non-carbohydrate precursors.

In yet another embodiment, the invention provides a synergistic nutritional composition comprising a therapeutically effective amount of biotin present in a range of 10-10000 mcg of the total composition.

In another embodiment, the invention provides a nutritional composition comprising manganese salt chelate, wherein effective amount of manganese salt chelate acts as a catalyst that improves pyruvate carboxylase enzymatic activity or kinetics and thus increase the rate of anaplerotic reaction.

In the instant invention, manganese salt chelate cofactor is a non-protein chemical compound or a metallic ion catalyst or a substance that increases the rate of a chemical reaction for production of oxaloacetate. More particularly, it is a benefactor ion that assists in biochemical transformations of pyruvate to oxaloacetate.

In yet another embodiment, the invention provides a synergistic nutritional composition comprising a therapeutically effective amount of manganese salt in a range of 0.5-100 mg of the total composition. The manganese salt is used as a chelating agent.

Further, manganese is present in many different forms, including but not limited to, amino acid chelates such as manganese bisglycinate chelate, manganese glycinate chelate, and manganese aspartate and non-amino acid chelate forms such as manganese gluconate, manganese picolinate, manganese sulphate, manganese citrate, and manganese chloride.

In another embodiment, the invention provides a synergistic anaplerotic effect by administering exogenous biotin-manganese complex and oxaloacetate, wherein mitochondrial oxaloacetate production is enhanced by administering exogenous biotin-manganese complex and cytosolic oxaloacetate level is balanced by exogenous effective amount of oxaloacetate.

According to the invention, the administration of effective amount of exogenous biotin-manganese complex enriches inner mitochondrial production of oxaloacetate through pyruvate carboxylation, and exogenous oxaloacetate ameliorates depleted cytosolic concentration of oxaloacetate.

Notably, the oxaloacetate formed in the cytosol is returned to the mitochondria. As the inner mitochondrial membrane is impermeable to oxaloacetate, it needs bypass reactions called shuttle or cleavage pathway that substantially improve NAD level.

First, oxaloacetate is reduced to malate by NADH in the cytosol.

Subsequently, the malate is oxidatively decarboxylated by an NADP$^+$-linked malate enzyme to form pyruvate.

The pyruvate formed in this reaction readily enters mitochondria, where it is carboxylated to oxaloacetate by pyruvate carboxylase catalyzed by biotin-Mn complex (FIG. 1)

Wherein Pi is inorganic phosphate, i.e., the phosphate released when ATP is hydrolyzed to ADP.

The sum of these three reactions is

Similarly, the exogenous OAA enters in Krebs cycle through citrate shuttle and thus provides electrons for ATP formation in ETC (FIG. 2).

In view of the above, the overall reactions are anaplerotic, wherein the combined density of oxaloacetate is enhanced through mitochondrial and cytosolic replenishment pathway that consequently increases NAD+level and generates ATP molecules through ETC.

In yet another embodiment, the invention relates to synergistic nutritional compositions comprising a combination of oxaloacetate salt present in a range of 1-500 mg of the total composition [equivalent to oxaloacetic acid], biotin present in a range of 10 to 10000 mcg of the total composition and cofactor Mn in the form of chelate in a range of 1 to 100 mg of the total composition; along with pharmaceutically acceptable excipients/carriers.

In some preferred embodiment, the invention provides synergistic nutritional composition(s) for promoting intracellular ATP production in a subject in need thereof comprising a therapeutically active exogenous combination of stabilized oxaloacetate and biotin-manganese complex along with pharmaceutically acceptable excipients.

In another preferred embodiment, the invention provides a synergistic nutritional composition comprising a therapeutically active exogenous combination of a stabilized oxaloacetate and a biotin-manganese complex along with pharmaceutically acceptable excipients, wherein the stabilized oxaloacetate and the biotin-manganese complex or salts thereof are present in a weight ratio ranging from 1:0.01 to 1:0.2.

In another preferred embodiment, the invention provides method for enhancing cellular ATP efficiency in a subject in need thereof comprising orally administering a therapeutically effective amount of a nutritional composition comprising an exogenous synergistic blend of a stabilized oxaloacetate and a biotin-manganese complex or salts thereof along with pharmaceutically acceptable excipients, wherein the stabilized oxaloacetate and the biotin-manganese complex or salts thereof are present in a weight ratio ranging from 1:0.01 to 1:0.2.

In another preferred embodiment, the invention provides a synergistic nutritional composition comprising stabilized oxaloacetate and a biotin-manganese complex; wherein the stabilized oxaloacetate, biotin and manganese are present in a weight ratio ranging from 1:0.01:0.01 to 1:0.5:0.05.

In another embodiment, the invention provides a potent synergistic nutritional composition comprising stabilized oxaloacetate in a range of 1-500 mg of the total composition.

In a further embodiment, the stabilized oxaloacetate comprises a homogenous premix of a crystalline organic oxaloacetic acid and standardized ascorbic acid or vitamin C as an antioxidant, wherein the crystalline organic oxaloacetic acid to standardized ascorbic acid weight ratio is in a range of 1:1 to 1:2. In a preferred embodiment, the oxaloacetic acid and standardized ascorbic acid weight ratio is in a range of 1:1.2 to 1:1.8.

The term 'standardized ascorbic acid' refers to a supplement that provides a therapeutically effective concentration of ascorbic acid. Further, the standardized ascorbic acid comprises 1-250 mg of ascorbic acid.

In another embodiment, the invention provides a potent synergistic nutritional composition comprising a synergistic combination of stabilized oxaloacetate and biotin-manganese complex, wherein biotin is water soluble vitamin B complex and is present in a range of 1 to 10 mg of the total composition.

In yet another embodiment, manganese (Mn) chelate is manganese sulphate monohydrate salt.

In another embodiment, the manganese salt is a crystalline form of manganese (II) sulphate monohydrate containing 10% of elemental manganese and present in a range of 1-10 mg.

In a further embodiment the invention provides a synergistic nutritional composition of a biotin-manganese complex, wherein the biotin-manganese complex comprises a homogenous premix of a crystalline form of D-isomer of biotin and a crystalline manganese (II) sulphate monohydrate in a weight ratio ranging 1:0.1 to 1:1.

In yet another embodiment, the invention provides a method for enhancing cellular ATP efficiency in a subject in need thereof, the method comprising orally administering a therapeutically effective amount of a nutritional composition comprising an exogenous synergistic blend of stabilized oxaloacetate and a biotin-manganese complex or salts thereof along with pharmaceutically acceptable excipients; wherein the stabilized oxaloacetate, biotin and manganese salts thereof are present in a weight ratio ranging from 1:0.01:0.01 to 1:0.5:0.05.

In yet another embodiment, the invention provides a method for enhancing cellular ATP efficiency in a subject in need thereof, the method comprising orally administering a therapeutically effective amount of a nutritional composition comprising an exogenous synergistic blend of stabilized oxaloacetate, a crystalline form of D-isomer of biotin, and a crystalline manganese (II) sulphate monohydrate along with pharmaceutically acceptable excipients; wherein the stabilized oxaloacetate, the crystalline form of D-isomer of biotin and the crystalline manganese (II) sulphate monohydrate are present in the weight ratio ranging from 1:0.01:0.01 to 1:0.5:0.05.

In one more embodiment, the invention provides a synergistic nutritional composition comprising stabilized oxaloacetate present in a range of 50% to 96% by weight of the total composition.

In yet another embodiment, the stabilized oxaloacetate comprises a homogenous premix of a crystalline organic oxaloacetic acid and a standardized ascorbic acid, wherein the crystalline organic oxaloacetic acid is present in a range of 25% to 50% and the standardized ascorbic acid is present in a range of 20% to 60% of ascorbic acid by weight of the total homogenous premix.

In yet another embodiment, the invention provides a synergistic nutritional composition comprising a crystalline form of D-isomer of biotin, wherein D-isomer of biotin is present in a range of 0.1% to 10% by weight of the total composition.

In a further embodiment, the invention provides a synergistic nutritional composition comprising a crystalline manganese (II) sulphate monohydrate in a range of 0.1% to 5% by weight of the total composition.

In yet another embodiment, the invention provides a synergistic nutritional composition comprising stabilized oxaloacetate, crystalline form of D-isomer of biotin and crystalline manganese (II) sulphate monohydrate in the weight ratio ranging from 1:0.01:0.01 to 1:0.5:0.05.

In one embodiment, the invention provides a nutritional composition comprising a synergistic combination of a crystalline oxaloacetic acid, a standardized ascorbic acid, D-biotin and manganese sulphate in a weight ratio ranging from 1:1:0.1:0.01 to 1:2:0.5:0.1. D-isomer of biotin is also referred to as D-biotin.

In another embodiment, the invention provides a method for enhancing cellular ATP efficiency by administering a nutritional composition comprising a synergistic combination of crystalline organic oxaloacetic acid, standardized ascorbic acid, a crystalline form of D-isomer of biotin, crystalline manganese (II) sulphate monohydrate along with pharmaceutically acceptable excipients, wherein the crystalline organic oxaloacetic acid, the standardized ascorbic acid, the crystalline form of D-isomer of biotin and the crystalline manganese (II) sulphate monohydrate are present in a weight ratio ranging from 1:1:0.1:0.01 to 1:2:0.5:0.1.

In another embodiment, the invention provides a method for promoting intracellular ATP levels in a subject in need thereof comprising, orally administering a therapeutically effective amount of a nutritional composition comprising a synergistic combination of crystalline biotin-manganese and stabilized oxaloacetate with pharmaceutically acceptable excipients, wherein the stabilized oxaloacetate is present in a range of 50% to 96%, the crystalline form of D-isomer of biotin is present in a range of 0.1% to 20%; crystalline manganese (II) sulphate monohydrate is present in a range of 0.1% to 10% by weight of the total composition In yet another embodiment, the invention provides a synergistic nutritional composition comprising stabilized oxaloacetate and biotin-manganese complex, wherein the stabilized oxaloacetate is present in a range of 80% to 96% and the biotin-manganese complex is present in a range of 0.5% to 10% by weight of the total composition.

In yet another embodiment, the invention provides a synergistic nutritional composition comprising biotin-manganese complex, wherein the biotin-manganese complex comprises a homogenous premix of a crystalline form of D-isomer of biotin and a crystalline manganese (II) sulphate monohydrate present in a weight ratio ranging from 1:0.1 to 1:1.

In the present invention, the term 'combination therapy' or 'concomitant therapy' denotes the characteristics or inventive feature of the present composition, wherein the two active moieties performing simultaneous functions in systematic pathways without any deviation or overlapping of the mechanism, consequently, improve brain function.

In additional embodiment, the invention provides an additional bioenhancer to improve the bioavailability of the present composition by enhancing the absorption of active ingredients inside the body.

As used herein, the term "therapeutically effective amount" is intended to mean the amount of active compounds of the present invention to be effective for promoting intracellular ATP level. Particularly, ATP enhancement therapy i.e., enhancement of energy production is useful for subjects suffering from a mitochondrial defect, disorder, or disease. Mitochondrial diseases result from dysfunction of the mitochondria. When the mitochondria fails, less and less energy is generated within the cell and cell injury or even cell death will follow. If this process is repeated throughout the body, the life of the subject suffering from such dysfunction is severely compromised and is likely to result in muscle, brain, liver, and heart related disorders.

It is noteworthy that enhancing ATP through metabolic pathway improves pathological conditions of diseases in which a decrease in ATP relates to the pathological conditions such as cellular ageing, cellular damages, loss of cellular functions, apoptosis, necrosis, cell death. ATP enhances the immune system and thus improves the host's own defense mechanisms to eradicate the virus-infected cells and restore normal immune function.

According to the invention, the diseases of the mitochondria appear most often in organs that are very energy demanding such as the brain, heart, liver, skeletal muscles, kidney, and the endocrine and respiratory system. Symptoms of a mitochondrial disease may include loss of motor control, muscle pain, seizures, visual/hearing problems, hepatic and renal diseases, ophthalmic impairment, cardiac diseases, liver diseases, gastrointestinal disorders, swallowing difficulties and more.

In another embodiment, the synergistic composition of the present invention is non-toxic, cost effective, enriched with nutrients or biomolecules and provides safeguard against mitochondrial damage from harmful toxins, without any adverse effect.

Further, the present synergistic combination of and oxaloacetate and biotin-manganese complex is used in the treatment of metabolic diseases, diseases of mitochondrial dysfunction, mitochondrial disorders and stimulation of mitochondrial energy production.

The synergistic combination of present bioactive compounds are used in the treatment of cancer and the following hypoxia, ischemia, stroke, myocardial infarction, acute angina, an acute kidney injury, coronary occlusion and atrial fibrillation, or to avoid or counteract reperfusion injuries. In some embodiment, the invention provides a method for promoting cellular ATP level in subject suffering from ATP deficiency disorders, age-related metabolic disorders, mitochondrial dysfunctions, metabolic disorders, neurodegenerative diseases, cardiovascular diseases, bone related disorders or central nervous system diseases. The age-related decline in the ATP level reduces the capacity to induce apoptosis and promotes necrotic inflammation that may trigger several age-dependent disorders.

In another embodiment, the invention provides a stable, nutritional composition that improves or ameliorates 'energy metabolism' which is useful for treating ATP deficiency disorders such as metabolic disorders or dysfunctions including but not limited to neurodegenerative diseases, cardiovascular diseases, bone disorders, mental or CNS disorders, such as insulin restriction, diabetes, obesity, hormonal imbalance in women, premenstrual syndrome (PMS), premenstrual dysphoric disorder (PMDD), cognitive disorders, endocrine disorders, traumatic brain injury, stroke, subarachnoid hemorrhage (SAH), ischemia, Alzheimer's and Parkinson's Diseases, traumatic spinal cord or traumatic brain injury (TBI), brain inflammation, insulin resistance, brain cancer, brain damage, heart and kidney diseases, caloric restriction inflammatory and like thereof.

In another embodiment, the metabolic disorder is selected from the group consisting of metabolic syndrome, insulin-deficiency or insulin-resistance related disorders, diabetes mellitus, glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system, obesity, cardiovascular diseases, high cholesterol, elevated triglycerides, asthma, heart attack, osteoarthritis, neurodegeneration, gallbladder disease, syndrome X, inflammatory and immune disorders, atherogenic dyslipidemia and cancer.

In yet another embodiment, the invention provides a method of treating a subject suffering from diseases of mitochondrial dysfunction or disease related to mitochondrial dysfunction, the method comprising administering to the subject an effective amount of the present synergistic nutritional composition to enhance the mitochondrial function.

The 'subject in need thereof' pertains to a subject preferably mammal, more preferably a human, wherein the subject is an infant and or an adult human. The subject may also include patients bearing pre-existing or onset symptoms of metabolic disorders, such as cardiovascular diseases and neurodegenerative diseases. Further, the subject may be a healthy person, who can be administered the present composition under preventive therapy.

The term "pharmaceutically acceptable salt" refers to a salt prepared from pharmaceutically acceptable non-toxic acids or bases, metal ions, minerals, chelates, complex, esters, sulphate, hydrate, oxide, amines which are well known in the art.

In a further embodiment, the present nutritional composition is used to normalize metabolic function in the subject in need thereof. Particularly, the remedy is administered either to prevent occurrence or pre-existing or onset cause of metabolic disorders.

As used herein, the term "specific or effective amount" is intended to mean the therapeutically effective dose of instant bioactive compounds namely biotin, manganese and oxaloacetic combined with each other to give synergy to the composition, which is otherwise not obtained by use of single ingredient of the composition.

Particularly "therapeutically effective amount" is an amount that reduces the risk, potential, possibility or occurrence of a disease or disorder, or provides advanced alleviation, mitigation, and/or reduction or restoration of at least one indicator/biomarker (e.g., blood or serum CRP level), and/or minimizes at least one clinical symptom of age-related metabolic disorders.

In the context of the present invention, the terms "treatment" and the like refer to alleviation, facilitation, mitigation, prophylaxis, attenuation, management, regulation, modulation, control, minimization, lessening, decrease, down regulation, up regulation, moderation, optimization, prevention, inhibition, stabilization, amelioration, reversal, boosting, normalization, induction, trigger cure, or healing of age-related cellular ATP decline.

Notably, the present synergistic composition is non-hazardous, non-toxic, and safe for human consumption without any side effects. Therefore, the present composition is also used under preventive therapy in healthy subjects.

In another embodiment, the invention relates to a synergistic composition prepared in a manner well known in the pharmaceutical art, and administered by a variety of routes, depending upon whether local or systemic treatment is desired and upon the area to be treated. The preferable route of administration includes but is not limited to sublingual, rectal, topical, parenteral, nasal, or oral. Therapeutic (prescription) supplements are generally administered by the oral, parenteral, or nasal routes for curing mitochondrial diseases. The therapeutic administration of the compositions of the present invention may be in conjunction with other therapies.

In one embodiment, the present synergistic nutritional composition is administered to a subject in a form suitable for oral use, such as a tablet, capsule (in the form of delayed release, extended release, sustained release, enteric coated release); hard gelatin capsules, soft gelatin capsules in an oily vehicle, granulate for sublingual use, effervescent tablets, aqueous or oily solution, suspension or emulsion, encapsulate, matrix, coat, beadlets, nanoparticles, caplet, granule, particulate, agglomerate, spansule, chewable tablet, lozenge, troche, solution, suspension, rapidly dissolving film, elixir, gel, as tablets, pellets, granules, capsules, lozenges, aqueous or oily solutions, suspensions, emulsions, sprays or reconstituted dry powdered form with a liquid medium or syrup. In another embodiment, the composition is formulated for parenteral use including intravenous, subcutaneous, intramuscular, intravascular, infusion, intraperitoneal, intracerebral, intracerebroventricular, or intradermal routes of administration. Further, the present synergistic composition is also useful for nasal administration through ion liquid spray device, nasal spray, intranasal spray device, nano-nasal spray, saline spray and like thereof.

In another embodiment, the pharmaceutically acceptable carriers, diluents or excipients are selected from the group consisting of an adjuvant, a carrier, an excipient, a glidant, a sweetening agent, a diluent, a preservative, a dye/colorant, a flavor enhancer, a surfactant, a wetting agent, a dispersing agent, a suspending agent, a stabilizer, an isotonic agent, a solvent, an emulsifier, or an encapsulating agent, such as a liposome, cyclodextrins, encapsulating polymeric delivery systems or polyethylene glycol matrix, which is acceptable for use in the subject, preferably humans. Excipients also include anti adherents, antioxidants, binders, coatings, compression aids, disintegrants, dyes (colors), emollients, emulsifiers, fillers (diluents), film formers or coatings, fragrances, glidants (flow enhancers), lubricants, preservatives, sorbents, suspending or dispersing agents, sweeteners, surfactant, anticaking agent, food additives, or waters of hydration.

In another embodiment of the invention, the diluents are selected from starches, hydrolyzed starches, partially pregelatinized starches, anhydrous lactose, cellulose powder, lactose monohydrate, sugar alcohols such as sorbitol, xylitol and mannitol, silicified microcrystalline cellulose, ammonium alginate, calcium carbonate, calcium lactate, dibasic calcium phosphate (anhydrous/dibasic dehydrate/tribasic), calcium silicate, calcium sulphate, cellulose acetate, corn starch, pregelatinized starch, dextrin, O-cyclodextrin, dextrates, dextrose, erythritol, ethyl cellulose, fructose, fumaric acid, glyceryl palmitostearate, magnesium carbonate, magnesium oxide, maltodextrin, maltose, medium-chain triglycerides, polydextrose, polymethacrylates, sodium alginate, sodium chloride, sterilizable maize, sucrose, sugar spheres, talc, trehalose, xylitol, vehicles like petrolatum, dimethyl sulfoxide and mineral oil or the like.

In a preferred embodiment of the invention, the diluent in the composition/formulation is present in a range of 1% to 30% by weight of the total composition/formulation.

In yet another embodiment of the invention, the binder is selected from disaccharides such as sucrose, lactose, polysaccharides and their derivatives like starches, cellulose, or modified cellulose such as microcrystalline cellulose and cellulose ethers such as hydroxypropyl cellulose (HPC); hydroxypropyl methyl cellulose (HPMC); sugar alcohols such as xylitol, sorbitol, or mannitol; protein like gelatin; synthetic polymers such as polyvinylpyrrolidone (PVP), polyethylene glycol (PEG), starch, acacia, agar, alginic acid, calcium carbonate, calcium lactate, carbomers, carboxymethylcellulose sodium, carrageenan, cellulose acetate phthalate, chitosan, co-povidone, corn starch, pregelatinized starch, cottonseed oil, dextrates, dextrin, dextrose, ethyl cellulose, guar gum, hydrogenated vegetable oil, mineral oil, hydroxyethyl cellulose, hydroxymethyl cellulose, hydroxyl ethyl methyl cellulose, hydroxypropyl cellulose, inulin, cellulose, methyl cellulose, polyvinylpyrrolidone and polyethylene glycol, lactose, liquid glucose, hypromellose, magnesium aluminum silicate, maltodextrin, maltose, methylcellulose, microcrystalline cellulose, pectin, poloxamer, polydextrose, polymethacrylates, povidone, sodium alginate, stearic acid, sucrose, sunflower oil, various animal vegetable oils, and white soft paraffin, paraffin, flavorants, colorants and wax.

In a preferred embodiment of the invention, the binder in the composition/formulation is present in a range of 0.1 to 40% by weight of the composition/formulation.

In a further embodiment of the invention, the lubricant is selected from magnesium stearate, zinc stearate, calcium stearate, glycerin monostearate, glyceryl behenate, glyceryl palmitostearate, hydrogenated castor oil, hydrogenated vegetable oil, light mineral oil, magnesium lauryl sulphate, medium-chain triglycerides, mineral oil, myristic acid, palmitic acid, poloxamer, polyethylene glycol, sodium benzoate, sodium chloride, sodium lauryl sulphate, sodium stearyl fumarate, stearic acid, talc, potassium, or sodium benzoate or the like.

In a preferred embodiment of the invention, the lubricant in the composition/formulation is present in a range of 0.1% to 5.0% by weight of the total composition/formulation.

In another embodiment of the invention, the solubilizing agent is selected from polysorbate 80, sodium lauryl sulphate, anionic emulsifying wax, nonionic emulsifying wax, glyceryl monooleate, phospholipids, polyoxyethylene alkyl ethers, polyoxyethylene castor oil derivatives, polyoxyethylene sorbitan fatty acid esters, polyoxyethylene stearates, polyoxylglycerides, sorbitan esters, triethyl citrate, vitamin E, polyethylene glycol succinate, microcrystalline cellulose, carboxymethylcellulose sodium, diethanolamine, ethylene glycol palmitostearate, glycerin monostearate, hypromellose, hypromellose, acetate succinate, lecithin, polyethylene alkyl ethers, aluminum oxide, poly(methylvinyl ether/maleic anhydride), calcium carbonate, crospovidone, cyclodextrins, fructose, hydroxypropyl betadex, oleyl alcohol, povidone, benzalkonium chloride, benzethonium chloride, benzyl alcohol, benzyl benzoate, cetylpyridinium chloride, inulin, meglumine, poloxamer, pyrrolidone, sodium bicarbonate, starch, stearic acid, sulfobutylether beta cyclodextrin, tricaprylin, triolein, docusate sodium, glycine, alcohol, self-emulsifying glyceryl monooleate, cationic benzethonium chloride, cetrimide, xanthan gum, lauric acid, myristyl alcohol, butylparaben, ethylparaben, methylparaben, propylparaben, sorbic acid or the like.

In an embodiment of the invention, the amount of solubilizing agent or surfactant in the composition/formulation ranges from 0.1% to 10% by weight of the composition/formulation. In a preferred embodiment of the invention, the solubilizing agent or surfactant is present in a range of 0.1% to 5.0% by weight of the composition/formulation.

In an embodiment of the invention, the glidant is selected from colloidal silicon dioxide, magnesium stearate, fumed silica (colloidal silicon dioxide), starch, talc, calcium phosphate tribasic, cellulose powdered, hydrophobic colloidal silica, magnesium oxide, zinc stearate, magnesium silicate, magnesium trisilicate, silicon dioxide or the like.

In another embodiment of the invention, the glidant in the composition/formulation is present in a range of 0.1% to 5.0% by weight of the total composition/formulation.

In one embodiment of the invention, the stabilizers are selected from the group consisting of alginate, agar, carrageen, gelatin, guar gum, gum arabic, locust bean gum, pectin, starch, xanthan gum, trehalose and likewise.

In a preferred embodiment of the invention, the stabilizer in the composition/formulation is present in a range of 0.1% to 8.0% by weight of the total composition/formulation.

In one embodiment of the invention, the solvent is selected from water, alcohol, isopropyl alcohol, propylene glycol, mineral oil, benzyl alcohol, benzyl benzoate, flavored glycol, carbon dioxide, castor oil, corn oil (maize), cottonseed oil, dimethyl ether, albumin, dimethylacetamide, ethyl acetate, ethyl lactate, medium-chain triglycerides, methyl lactate, olive oil, peanut oil, polyethylene glycol, polyoxyl, castor oil, propylene carbonate, pyrrolidone, safflower oil, sesame oil, soybean oil, sunflower oil, water-miscible solvents, organic polar or non-polar solvents or mixtures thereof.

In a preferred embodiment of the invention, the solvent in the composition/formulation is used in a quantity sufficient to make the weight of the composition/formulation 100% by weight.

The additional additives include a polymer, a plasticizer, a sweetener, and a powdered flavor, a preservative, a colorant, a surfactant, and other excipients. The powdered flavor composition includes a flavourant associated with a solid carrier. Coating materials such as synthetic polymers, shellac, corn protein (zein) or other polysaccharides, gelatin, fatty acids, waxes, shellac, plastics, and plant fibers and like thereof are used. In a preferred embodiment of the invention, the additives are used in a range of 1 to 20% w/w of unit dose.

In another embodiment, the invention provides a synergistic nutritional composition comprising an exogenous blend of biotin-Mn complex and stabilized OAA along with pharmaceutical excipients, wherein pharmaceutical excipients are selected from a diluent, a binder, a surfactant, a lubricant, a glidant, an additive, a stabilizer, or mixtures thereof.

In yet another embodiment, the invention provides a synergistic nutritional composition comprising a therapeutic blend of a biotin-manganese complex and a stabilized oxaloacetate along with pharmaceutical excipients, wherein the pharmaceutical excipients are selected from a diluent, a binder, a lubricant, a glidant, an additive, a surfactant, a stabilizer or mixtures thereof. In a preferred embodiment, the diluent is present in a range of 1 to 30%; the binder present is present in a range of 0.1 to 25%; the lubricant is present in a range of 0.1 to 5.0%; the glidant is present in a range of 0.1 to 5.0%; the additive is present in a range of 1 to 10%; the surfactant is present in a range of 0.1 to 5.0%; the stabilizer is present in a range of 0.1 to 5.0% by weight of total composition.

In a further embodiment, the present composition is formulated in the form of age-appropriate pediatric oral dosage forms such as syrup, minitablets, chewable formulations, orodispersible films and orodispersible tablets.

In a preferred embodiment, the present medicinal composition/formulation is formulated for oral administration. Specifically, the solid medicinal compositions, are in the form of tablets, capsules, pills, hard capsules filled with liquids or solids, soft capsules, sachets, powders, granules, suspensions, solutions, or modified release formulations. Formulations of the present invention suitable for oral administration are presented as discrete units such as capsules (e.g., soft-gel capsules, hard-gel capsule), cachets or tablets each containing a predetermined amount of the active ingredient; as a powder or granules; as a solution or a suspension in an aqueous liquid or a non-aqueous liquid, syrup; or as an oil-in-water liquid emulsion or a water-in-oil liquid emulsion.

The magnitude of a prophylactic or therapeutic dose typically varies with the nature and severity of the condition to be treated and the route of administration. The dose, and perhaps the dose frequency, will also vary according to the age, body weight and response of the individual patient. In general, the total daily dose (in single or divided doses) ranges from about 1 mg per day to about 5000 mg per day. In a preferred embodiment, the total daily dose ranges from about 10 mg per day to about 1000 mg per day.

In a further embodiment, the invention provides synergistic nutritional compositions comprising a specific combination of stabilized oxaloacetate and biotin-manganese complex along with pharmaceutically acceptable excipients or carriers, wherein the effective unit dose for oral administration is in a range of 50 to 800 mg. Particularly, the effective unit dose of the composition is in a range of 20 mg to 500 mg.

In one embodiment, oral administration of an effective dose of the composition enhances the intracellular ATP level by 46% over normal control.

It is further recommended that children, patients over 60 years old, initially receive low doses and that the dosage be titrated based on individual physiological responses and/or pharmacokinetics. It can be necessary to use dosages outside these ranges in some cases, as will be apparent to those in the art. The present composition can be used as infant formula as well as adult formula by varying the concentration of active ingredients. Further, it is noted that the dietician or nutritionist or certified physician knows how and when to interrupt, adjust or terminate therapy in conjunction with an individual patient's response.

The use of any and all examples, or exemplary language (e.g., "such as") provided herein, is intended merely to better illuminate the invention and does not pose a limitation on the scope of the invention unless otherwise claimed.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention may be further illustrated by the following examples, which are for illustrative purposes only and should not be construed as limiting the scope of the invention in anyway. The present invention is not to be limited in terms of the particular embodiments described in this application, which are intended as single illustrations of individual aspects of the invention. Functionally equivalent compositions and treatments within the scope of the invention, in addition to those enumerated herein, will be apparent to those skilled in the art from the foregoing description and examples. Such modifications and variations are intended to fall within the scope of the appended claims. The contents of each reference, patent and patent application cited in this application is hereby incorporated by reference in its entirety.

EXAMPLES

Example-1 i. Composition 1: Synergistic blend

| Ingredients | w/w % |
| --- | --- |
| Stabilized oxaloacetate (A) | 50-96% |
| Biotin (B) | 0.1-10.0% |
| Manganese sulphate (C) | 0.1-5.0% | ii. Composition 2: Tablet/Capsule

| Ingredients | w/w % unit dose |
| --- | --- |
| Stabilized oxaloacetate - [A] | 60-95% |
| D-Biotin- [B] | 1-5% |
| Manganese sulphate- [C] | 0.1-0.8% |
| Excipients | 5-20% |
| Average Weight (%) | 100% |
| Average weight in mg | 150-200 mg | iii. Composition 3: Tablet/Capsule

| Ingredients | w/w % unit dose |
| --- | --- |
| Oxaloacetic acid | 30-40% |
| D-Biotin | 3-5% |
| Manganese sulphate monohydrate | 0.5-0.8% |
| Standardized Ascorbic acid | 50-60% |
| Diluents | 1-10% |
| Binders | 0.5-5% |
| Glidants | 0.5-5% |
| Lubricants | 0.5-5% |
| Stabilizers | 0.1-10% |
| Additives | 1-10% |
| Solvents | QS | iv. Composition 4: Tablet/Capsule

| Ingredients | mg per unit dose |
| --- | --- |
| Oxaloacetic acid | 50 |
| Standardized Ascorbic acid | 75 |
| D-Biotin | 5 |
| Manganese sulphate monohydrate | 1 |
| Silicon dioxide | 1-10 |
| Hydroxypropyl Methylcellulose | 1-10 |
| Microcrystalline Cellulose | 1-20 |
| Zinc Stearate | 1-10 |
| PVP K-30 | 5-10 |
| Cyclodextrin | 1-10 |
| Polysorbate 80 | 1-10 |
| Mannitol | 1-20 |
| Propylene Glycol | QS |
| Water | QS |
| Average weight | 140-160 mg | v. Composition 5: Tablet/Capsule

| Ingredients | mg per unit dose |
| --- | --- |
| Oxaloacetic acid | 50 |
| Standardized Ascorbic acid | 75 |
| D-Biotin | 5 |
| Manganese sulphate monohydrate | 5 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium citrate | 2-10 |
| PVP K-30 | 5-10 |
| Talc | 1-10 |
| Tween 80 | 1-10 |
| Mannitol | 5-20 |
| Alcohol | QS |
| Water | QS |
| Average weight | 150-175 mg | vi. Composition 6: Tablet/Capsule

| Ingredients | mg per unit dose |
| --- | --- |
| Oxaloacetic acid | 50 |
| Standardized Ascorbic acid | 50 |
| D-Biotin | 5 |
| Manganese sulphate monohydrate | 5 |
| Sodium ascorbate | 1-10 |
| Microcrystalline Cellulose | 2-20 |
| Silicon dioxide | 5-15 |
| Hydroxypropyl Methylcellulose | 2-10 |
| Magnesium citrate | 2-10 |
| PVP K-30 | 5-10 |

-continued vi. Composition 6: Tablet/Capsule

| Ingredients | mg per unit dose |
| --- | --- |
| Talc | 1-10 |
| Tween 80 | 1-10 |
| Mannitol | 5-20 |
| Alcohol | QS |
| Water | QS |
| Average weight | 150-175 mg | vii. Composition 7: Tablet/Capsule

| Ingredients | mg per unit dose |
| --- | --- |
| Oxaloacetic acid | 50 |
| Standardized Ascorbic acid | 75 |
| D-Biotin | 10 |
| Manganese sulphate monohydrate | 5 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |
| Water | QS |
| Average weight | 175-250mg | viii. Composition 8: Tablet/Capsule

| Ingredients | mg per unit dose |
| --- | --- |
| Oxaloacetic acid | 100 |
| Standardized Ascorbic acid | 50 |
| D-Biotin | 10 |
| Manganese sulphate monohydrate | 2 |
| Microcrystalline Cellulose | 1-10 |
| Silicon dioxide | 1-10 |
| Hydroxypropyl Methylcellulose | 1-10 |
| Magnesium Stearate | 2-10 |
| Polyvinylpyrrolidone | 1-10 |
| Talc | 1-10 |
| Polysorbate 20 | 1-10 |
| Mannitol | 1-10 |
| IPA | QS |
| Water | QS |
| Average weight | 200-250 mg |

Example 2: Cell Line Study

To Assess the In Vitro Potential of Test Substances on Increasing the Cellular ATP Levels in Human Hepatocyte Cell Line The test substances were evaluated for their in vitro effect on cellular energy by measuring cellular ATP levels in human Hepatocytes (HepG2) cell line. In the given experimental conditions, treatment with the test substances improved cellular ATP levels in vitro [*J Immunol Methods;* 1986; 89: 271-277]; [*Proc Nal Acad Sci USA;* 2009; 106: 15651-15656].

Procedure i. Outline of the Method

The in vitro cytotoxicity was performed on HepG2 (Human Hepatocyte) cell line to find a non-toxic concentration of the test substances by MTT assay and the potential of test substances to increase the cellular ATP levels was evaluated by kit method.

ii. Preparation of Test Solution

For test substance ABC, the test substances were combined in the weight ratio of 1:0.05:0.01. A weight of about 10 mg of ABC was dissolved in 100 µl of DMSO and the volume was made up to 1 ml with DMEM-HG (Dulbecco's Modified Eagle Medium High Glucose). For individual test substances A, B and C, about 10 mg of all the test substances were weighed and separately dissolved with 100 µl of DMSO and volume was made up with DMEM-HG supplemented with 2% inactivated FBS to obtain a stock solution of 1 mg/ml concentration. The samples were further sterilized by 0.22 syringe filtration. Serial two-fold dilutions were prepared from the stock for carrying out further studies.

iii. Cell Line and Culture Medium:

Cell line was cultured in DMEM-HG supplemented with 10% inactivated Fetal Bovine Serum (FBS), penicillin (100 IU/ml), streptomycin (100 µg/ml) and amphotericin B (5 µg/ml) in a humidified atmosphere of 5% $CO_2$ at 37° C. until confluent. The cells were dissociated with TPVG solution (0.2% trypsin, 0.02% EDTA, 0.05% glucose in PBS). The stock cultures were grown in 25 $cm^2$ culture flasks and all experiments were carried out in 96 well microtitre plates (Tarsons India Pvt. Ltd., Kolkata, India).

iv. Cytotoxicity Studies

The monolayer cell culture was trypsinized and the cell count was adjusted to $1.0 \times 10^5$ cells/ml using DMEM-HG containing 10% FBS. To each well of the 96 well microtitre plate, 0.1 ml of the diluted cell suspension was added. After 24 hours, when a partial monolayer was formed, the supernatant was flicked off, the monolayer was washed once with medium and 100 µl of different concentrations of test substances were added. The plate was then incubated at 37° C. for 72 hours in a 5% $CO_2$ atmosphere, and microscopic examination was carried out with observations being noted at a 24-hour interval.

iv. MTT Assay

After 72 hours of incubation, the drug solutions in the wells were discarded and 50 µl of MTT in PBS was added to each well. The plate was gently shaken and incubated for 3 hours at 37° C. in a 5% $CO_2$ atmosphere. The supernatant was removed and 100 µl of 2-propanol was added and the plate was gently shaken to solubilize the formed formazan. The absorbance was measured using a microplate reader at a wavelength of 540 nm. The percentage growth inhibition was calculated using the standard formula. The concentration of test substances needed to inhibit the growth of the cell by 50% i.e., $CTC_{50}$ values were generated from the dose-response curves.

v. Estimation of Cellular Respiration by Measuring Cellular ATP Levels

HepG2 cells were trypsinized from stock culture flasks and the cell count was adjusted to $1.0 \times 10^5$ cells/ml to obtain a cell suspension that was seeded into a 6-well plate. After 24 hours, cell cultures achieved 70-80% confluency and were treated with different nontoxic concentrations of test substances. After 2 hours of treatment, the plate was washed with phosphate buffer saline. The cellular ATP level determination was performed according to the instructions given in the kit manual (SIGMA, #MAK190). At the end of the experiment, the optical density was read at 570 nm using microplate reader. From the absorbance values, the cellular ATP levels were estimated using kit protocol and the concentration of cellular ATP in treated groups were determined in comparison to the control groups.

vi. Study Design

TABLE 1

Group, dose and treatment

| Group No. | Group | Dose and Treatment | Parameters Analyzed |
|---|---|---|---|
| G1 | Cell Control | No treatment | Cellular ATP levels |
| G2 | Positive Control ($H_2O_2$- 20 μM) | Cells treated with $H_2O_2$ | |
| G3 | Standard (Resveratrol) 100 μg/ml | Cells treated with Resveratrol | |
| G4 | Stabilized Oxaloacetate (500 μg/ml) | Cells treated with Stabilized Oxaloacetate | |
| G5 | D-Biotin (500 μg/ml) | Cells treated with D-Biotin | |
| G6 | Manganese Sulphate Monohydrate (500 μg/ml) | Cells treated with Manganese Sulphate | |
| G7 | Oxaloacetate + Biotin -Mn Complex (500 μg/ml) | Cells treated with Oxaloacetate + Biotin -Mn Complex | |

TABLE 2

Cytotoxicity properties of test substances against HepG2 cell line

| Sl. No | Name of Test Compound | Test Conc. (μg/ml) | % Inhibition | CTC 50 in μg/ml |
|---|---|---|---|---|
| 1. | G4 Stabilized Oxaloacetate (A) | 1000 | 40.42 ± 1.22 | >1000 |
| | | 500 | 34.40 ± 2.20 | |
| | | 250 | 23.81 ± 2.25 | |
| | | 125 | 16.61 ± 0.82 | |
| | | 62.5 | 10.65 ± 0.84 | |
| 2. | G5 D-Biotin (B) | 1000 | 47.62 ± 1.45 | >1000 |
| | | 500 | 42.86 ± 1.29 | |
| | | 250 | 31.25 ± 1.17 | |
| | | 125 | 25.06 ± 0.81 | |
| | | 62.5 | 6.13 ± 3.48 | |
| 3. | G6 Manganese-Sulphate (C) | 1000 | 59.35 ± 0.63 | 558.91 ± 6.22 |
| | | 500 | 48.75 ± 0.18 | |
| | | 250 | 42.44 ± 0.81 | |
| | | 125 | 35.54 ± 0.47 | |
| | | 62.5 | 30.00 ± 0.54 | |
| 4. | G7 [A:B:C] [1:0.05:0.01] | 1000 | 39.51 ± 2.53 | >1000 |
| | | 500 | 22.84 ± 3.31 | |
| | | 250 | 15.43 ± 1.52 | |
| | | 125 | 8.81 ± 1.47 | |
| | | 62.5 | 3.85 ± 2.25 | |

TABLE 3

Effect of test substances on cellular ATP levels in HepG2 cells

Figure 3:
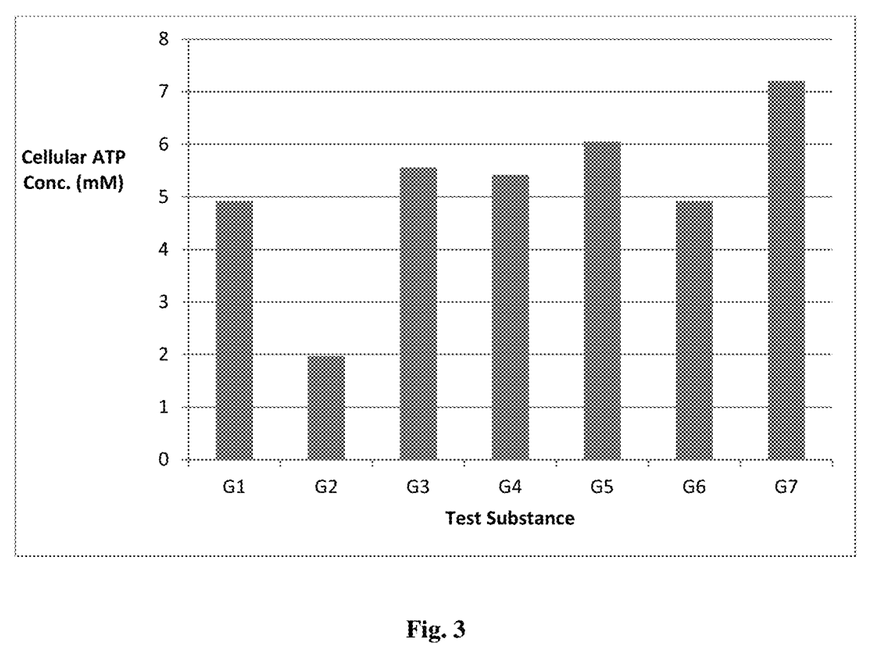
FIG. 3 illustrates the effect of test substances on cellular ATP concentration in different treated groups [concentration of ATP levels in mM] {G1—Normal control, G2—Positive Control ($H_2O_2$— 20 µM), G3—Standard (Resveratrol) 100 µg/ml, G4—Stabilized Oxaloacetate (500 µg/ml), G5—D-Biotin (500 µg/ml), G6—Manganese Sulphate Monohydrate (500 µg/ml), G7—Oxaloacetate+Biotin+Manganese Sulphate Monohydrate (500 µg/ml) [1:0.05:0.01]}.
Figure 4:
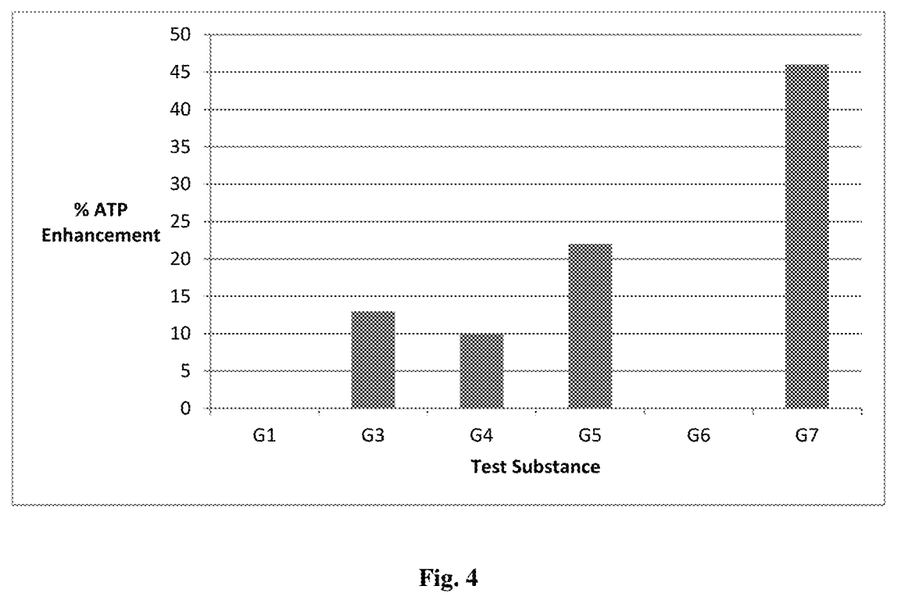
FIG. 4 illustrates the percentage enhancement of ATP in treated groups over control {G1—Normal control, G2—Positive Control ($H_2O_2$— 20 μM), G3—Standard (Resveratrol) 100 μg/ml, G4-Stabilized Oxaloacetate (500 μg/ml), G5—D-Biotin (500 μg/ml, G6—Manganese Sulphate Monohydrate (500 μg/ml), G7—Oxaloacetate+Biotin+Manganese Sulphate Monohydrate (500 g/ml) [1:0.05:0.01]}.
Figure 5:
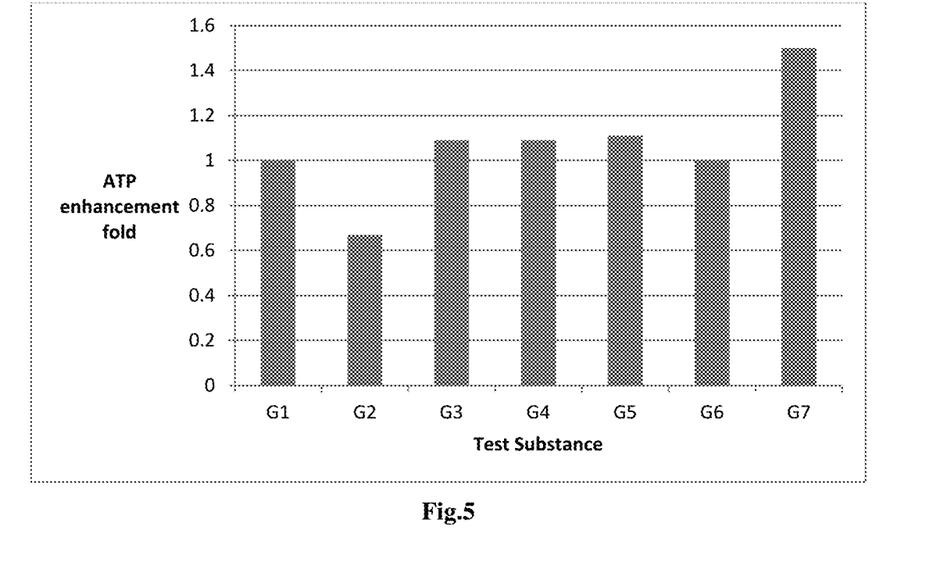
FIG. 5 illustrates the ATP enhancement of test substances over control {G1—Normal control, G2—Positive Control ($H_2O_2$— 20 μM), G3—Standard (Resveratrol) 100 μg/ml, G4—Stabilized Oxaloacetate (500 μg/ml), G5—D-Biotin (500 μg/ml), G6—Manganese Sulphate Monohydrate (500 μg/ml), G7—Oxaloacetate+Biotin+Manganese Sulphate Monohydrate (500 μg/ml) [1:0.05:0.01]}.

| Group No | Name of the test substances | Test Conc. in μg/ml | OD values (treated)- @ 570 nm | Cellular ATP Conc. (mM) | % ATP Enhancement | ATP enhancement fold |
|---|---|---|---|---|---|---|
| G1 | Control | — | 0.103 | 4.92 ± 0.29 | 00 | 1.00 |
| G2 | $H_2O_2$ | 20 μM | 0.069 | 1.97 ± 0.45 | — | 0.67 |
| G3 | Resveratrol | 100 μg/ml | 0.112 | 5.56 ± 0.37 | 13% | 1.09 |
| G4 | Oxaloacetic acid (A) | 500 μg/ml | 0.112 | 5.42 ± 0.25 | 10% | 1.09 |
| G5 | Biotin (B) | 500 μg/ml | 0.114 | 6.05 ± 0.33 | 22% | 1.11 |
| G6 | Manganese sulphate (C) | 500 μg/ml | 0.103 | 4.92 ± 0.13 | 00 | 1.00 |
| G7 | Oxaloacetic acid + Biotin + Manganese Sulphate (ABC) | 500 μg/ml | 0.154 | 7.21 ± 0.27 | 46% | 1.50 | vii. Discussion:

The test substances A, B, C and ABC were evaluated for their cytotoxicity with different concentrations ranging from 1000 µg/ml to 62.5 µg/ml. Non-toxic concentrations of the test substances were taken for further studies. The cellular ATP levels for the test substances were found to be 5.42±0.25 mM 6.05±0.33 mM, 4.92±0.13 mM and 7.21±0.27 mM for A, B, C and ABC [1:0.05:0.01] at the test concentrations respectively. No significant enhancement of cellular ATP levels over the control was found at a concentration of 500 µg/ml for test substances A, B, and C. However, the combination of A, B and C in a specific weight ratio of 1:0.05:0.01 showed significant enhancement of cellular ATP levels over the control with 46% cellular ATP level enhancement. Further, the enhancement of cellular ATP levels over the control was found to be 1.09, 1.11, 1.00, and 1.50 for A, B, C and ABC [1:0.05:0.01] at the test concentrations respectively.

CONCLUSION

The results indicate that the test substances increase cellular respiration in HepG2 cells. The test substance combination ABC in a weight ratio of 1:0.05:0.01 has exhibited a significant increase in cellular ATP levels over untreated control at the tested concentrations. The present synergistic nutritional composition after oral administration in effective dose amount enhances intracellular ATP level by 46%.

The invention claimed is:

1. A method for enhancing cellular ATP efficiency in a subject in need thereof, the method comprising:
   orally administering a therapeutically effective amount of a nutritional composition including an exogenous synergistic blend of a stabilized oxaloacetate and a biotin-manganese complex or salts thereof along with pharmaceutically acceptable excipients,
   wherein the stabilized oxaloacetate and the biotin-manganese complex or salts thereof are present in a weight ratio ranging from 1:0.01 to 1:0.2, and wherein
   the stabilized oxaloacetate comprises a homogenous premix of a crystalline organic oxaloacetic acid and a standardized ascorbic acid in a weight ratio of 1:1 to 1:2, and
   the biotin-manganese complex comprises a homogenous premix of a crystalline form of D-isomer of biotin and a crystalline manganese (II) sulphate monohydrate in a weight ratio of 1:0.1 to 1:1.

2. The method according to claim 1, wherein the stabilized oxaloacetate is present in a range of 50% to 96% by weight of the total composition.

3. The method according to claim 1, wherein the stabilized oxaloacetate, the crystalline form of D-isomer of biotin and the crystalline manganese (II) sulphate monohydrate are present in a weight ratio ranging from 1:0.01:0.01 to 1:0.5:0.05.

4. The method according to claim 1, wherein the crystalline form of D-isomer of biotin is present in a range of 0.1% to 10% by weight of the total composition.

5. The method according to claim 1, wherein the crystalline manganese (II) sulphate monohydrate is present in a range of 0.1% to 5% by weight of the total composition.

6. The method according to claim 1, wherein the nutritional composition includes:
   a synergistic combination of the crystalline organic oxaloacetic acid, the standardized ascorbic acid, the crystalline form of D-isomer of biotin, and the crystalline manganese (II) sulphate monohydrate along with pharmaceutically acceptable excipients, and
   the crystalline organic oxaloacetic acid, the standardized ascorbic acid, the crystalline form of D-isomer of biotin, and the crystalline manganese (II) sulphate monohydrate are present in a weight ratio ranging from 1:1:0.1:0.01 to 1:2:0.5:0.1.

7. The method according to claim 1, wherein the pharmaceutically acceptable excipients are selected from a group consisting of:
   a diluent present in a range of 1 to 30%;
   a binder present in a range of 0.1 to 25%;
   a lubricant present in a range of 0.1 to 5.0%;
   a glidant present in a range of 0.1 to 5.0%;
   an additive present in a range of 1 to 10%;
   a surfactant present in a range of 0.1 to 5.0%; and
   a stabilizer present in a range of 0.1 to 5.0% by weight of the total composition.

8. The method according to claim 1, wherein the composition enhances cellular ATP level in a subject suffering from ATP deficiency disorders, age-related metabolic disorders, mitochondrial dysfunctions, neurodegenerative diseases, cardiovascular diseases, bone related disorders or central nervous system diseases.

9. The method according to claim 8, wherein the ATP deficiency disorders are selected from a group consisting of insulin restriction, diabetes, obesity, hormonal imbalance in women, premenstrual syndrome (PMS), premenstrual dysphoric disorder (PMDD), cognitive disorders, endocrine disorders, traumatic brain injury, ischemia, Alzheimer's diseases, Parkinson's diseases, traumatic spinal cord or traumatic brain injury (TBI), brain inflammation, brain damage, bone disorders, caloric restriction, heart-attack, glucose intolerance, abnormal lipid metabolism, atherosclerosis, hypertension, cardiac pathology, stroke, non-alcoholic fatty liver disease, hyperglycemia, hepatic steatosis, dyslipidemia, high cholesterol, elevated triglycerides, asthma, osteoarthritis, neuro-degeneration, gallbladder disease, caloric restriction inflammatory and kidney diseases.

10. The method according to claim 1, wherein the subject is an infant and or an adult human.

* * * * *